US006991108B1

United States Patent
Rorato et al.

(10) Patent No.: US 6,991,108 B1
(45) Date of Patent: Jan. 31, 2006

(54) DEVICE FOR STORING OBJECTS

(75) Inventors: Gianni Rorato, Grenchen (CH); Silvin Jancic, Villmergen (CH); Marcel Suter, Kleindoettingen (CH)

(73) Assignee: Mathys Medizinaltechnik AG, Bettlach (CH)

(*) Notice: Subject to any disclaimer, the term of this patent is extended or adjusted under 35 U.S.C. 154(b) by 0 days.

(21) Appl. No.: 10/257,902

(22) PCT Filed: Apr. 17, 2000

(86) PCT No.: PCT/CH00/00221

§ 371 (c)(1),
(2), (4) Date: Jun. 9, 2003

(87) PCT Pub. No.: WO01/78619

PCT Pub. Date: Oct. 25, 2001

(51) Int. Cl.
*B65D 21/00* (2006.01)
*B65D 85/62* (2006.01)
(52) U.S. Cl. ............... 206/503; 206/570; 220/4.27; 220/23.83
(58) Field of Classification Search ............... 220/4.27, 220/324, 23.4, 23.8, 28.83; 206/363, 366, 206/369, 370, 372, 373, 501, 503, 505, 506, 206/499, 570, 571, 572, 349, 509; 422/297, 422/300
See application file for complete search history.

(56) References Cited

U.S. PATENT DOCUMENTS

| 4,109,789 | A | * | 8/1978 | Fattori et al. ............... 206/404 |
| 4,349,109 | A | * | 9/1982 | Scordato et al. ............ 206/562 |
| 5,174,453 | A |   | 12/1992 | Stoeffler |
| 5,628,970 | A | * | 5/1997 | Basile et al. ................ 422/297 |
| 5,732,821 | A |   | 3/1998 | Stone et al. |
| 5,950,828 | A | * | 9/1999 | Bal ............................ 206/370 |

FOREIGN PATENT DOCUMENTS

| DE | 93 03 604 U | 8/1993 |
| FR | 2 127 815 A | 10/1972 |
| FR | 2 497 089 A | 7/1982 |

* cited by examiner

*Primary Examiner*—Nathan J. Newhouse
*Assistant Examiner*—Harry Grosso
(74) *Attorney, Agent, or Firm*—Rankin, Hill, Porter & Clark LLP

(57) ABSTRACT

A device for storing surgical instruments and/or implants, the device including at least one dish-shaped instrument tray (4) and a sealable lid (1) that is located on the top (6) of the tray. Each instrument tray (4) has a base (9) with a preferably rectangular outline and lateral walls (16) that are attached and extend vertically relative to the base (9) from the base underside (7). The instrument trays (4) can be stacked. The lid (1) includes two displaceable closure mechanisms (3) having lower locking elements (12) that are directed towards the underside of the lid (13). In addition, each instrument tray (4) has displaceable locking device (10), with which an instrument tray (4) can be detachably fixed to an instrument tray (4) lying immediately below. The locking device (10) includes upper locking elements (11) that are directed towards the top (6) and lower locking elements (12) that are directed towards the underside (7). The lower locking elements (12) can be detachably engaged with the upper locking elements (11) and with the base (9) of the instrument tray (4) lying immediately below to simultaneously fix the lid (1) and several instrument trays (4) to each other.

12 Claims, 5 Drawing Sheets

DEVICE FOR STORING OBJECTS

Figure 1:
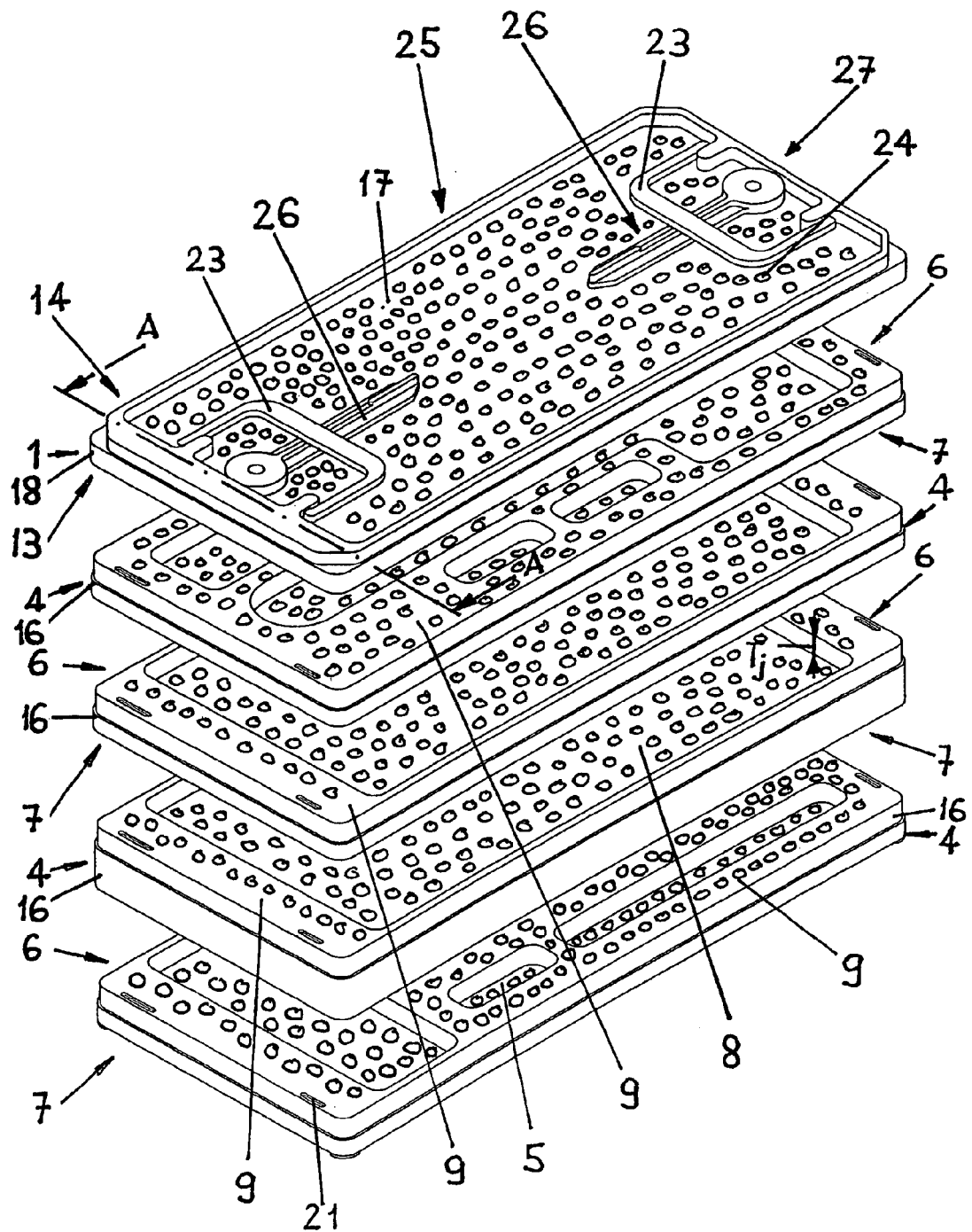

The invention concerns a device for storing objects, in particular surgical instruments and/or implants according to the preamble of patent claim 1.

Surgical instruments are arranged often in accordance with their purpose of application and stored together with the corresponding implants. These storage containers or instrument cases are usually so constructed, that the storage containers could be sterilised together with the surgical instruments and implants.

Such instrument cases comprise mostly a container, a plurality of insert trays that can be inserted into the container and a lockable lid with handles. The insert trays as well as the base of the container are usually provided with auxiliary means for the positioning of the instruments and implants. For the purpose of sterilisation the lateral walls and the base of the container, the lid and the insert trays are provided with passing through holes, which allow the distribution of the steam in the entire instrument case.

Such an instrument case for medical instruments and implants is known, for example, from U.S. Pat. No. 5,628,970 BASILE. This known instrument case comprises a container, an insert tray that can be inserted therein and a lid. On the base of the container as well as on the insert tray depressions and clamping jaws are provided, allowing a positioning and fastening of the instruments and of the implants. All three parts are provided with recessable handles and can be locked in the assembled state by means of a clamping lock provided on the lid. The base of the container, the insert tray and the lid have holes drilled through for ventilation.

It is a disadvantage of such instrument cases that the removal of an instrument or of an implant from the lowermost instrument tray or container base after the removal of the lid requires a consecutive removal of each instrument tray adjacent above, also requiring a correspondingly large storage area in the operating theatre. Furthermore, in the case of these embodiments with an outer shell, the heights of the individual instrument trays is to be so selected, that the stacked instrument trays reach up to the lid of the case so that when locked they would obtain the required pressure on the instrument tray via the lid. Otherwise the instrument trays will be thrown about in the outer shell when the case is being moved.

A further instrument case is known from FR 2 127 815 AESCULAP. The locking mechanism disclosed in this known document comprises clamps as well as protuberances on each instrument tray, whereby each clamp of an instrument tray provided below has to separately engage the protuberance on the top of the instrument tray or on the lid.

A further instrument case is also known from U.S. Pat. No. 5,174,453 STOEFFLER. In the device disclosed therein also each instrument tray has to be separately locked with the instrument tray adjacent above. The upward directed pins provided on the instrument trays pass through the holes of the instrument tray immediately adjacent above and locked or unlocked individually with the slides provided on the respective upper instrument tray.

It is a disadvantage of both devices mentioned above, that the lid as well as the stacked instrument trays cannot be locked or unlocked by a single central locking mechanism.

This is where the invention wants to provide remedy. The object of the invention is to produce an instrument case that makes a stacking and locking of a plurality of instrument trays possible without the necessity of inserting them into a container. In addition, the locking of the lid and of the instrument trays should be carried out synchronously and centrally by actuating two handles provided on the lid.

This objective is achieved by the invention with a device for storing objects, in particular surgical instruments and/or implants, having the features of claim 1.

The device according to the invention for storing surgical instruments and/or implants comprises at least one shell-shaped instrument tray and one lid that can be locked on the upper side of the instrument tray. Each instrument tray has a base with a preferably rectangular outline, an upper side that is essentially parallel to the base, an underside, as well as lateral walls that are provided on the base essentially perpendicularly. In addition each instrument tray can be stacked with a further instrument tray. The lid essentially comprises a cover plate having the same horizontal outline, has an upper side and an underside and comprises at least one displaceable locking mechanism with lower locking elements facing the underside of the lid for the purpose of fastening the lid on the upper side of an instrument tray. Furthermore, each instrument tray comprises displaceable locking means, by means of which each instrument tray can be detachably fastened with an instrument tray adjacent below. These locking means have upper locking elements facing the upper side of the instrument tray and lower locking elements facing the underside of the instrument tray. To secure the lid on an instrument tray as well as to secure a plurality of instrument trays relative one another, the lower locking elements can de detachably engaged with the upper locking elements and with the base of an instrument tray adjacent below. On this occasion the engagement of the lower locking elements with the upper locking mechanisms on the lid. The engagement of the lower locking elements with the base of the instrument tray adjacent below is carried out parallel to the base and serves the purpose of detachable securing of the lid as well as of one or a plurality of instrument trays relative one another and perpendicularly to their horizontal outline.

The advantage of these locking mechanisms and of the locking means executed in this manner is that a locking of the lid and of all instrument trays can be carried out centrally by actuating the handles provided on the lid.

In an embodiment of the device according to the invention the lateral walls of the instrument tray i have perpendicularly to the horizontal outline a height of $H_i$ and are outwardly cranked from the underside to a depth of $T_i$, so that there is a shoulder on the inside of the lateral walls at the depth of $T_i$, that in the case of stacked instrument trays rests on the base of the instrument tray adjacent below. Instead of resting on the shoulder situated on the internal side on the base of the instrument tray adjacent below, a development of the outwardly cranked lateral walls is also conceivable whereby the depth $T_i$ is so dimensioned that the underside of an instrument tray can rest on the shoulder of the instrument tray adjacent below and formed by the outward crank on the external side of the lateral walls. The advantage of these outward cranked lateral walls is to be seen in that the lower locking elements do not project past the underside of the lateral walls, so that each instrument tray has a level underside. Furthermore, the outward cranked lateral walls increase the resistance of the instrument tray against twisting.

The height $H_i$ may vary for the various instrument trays, whereas the depth $T_i$ is preferably standardised and is the same for all instrument rays. Consequently, the locking between the individual instrument trays is ensured.

Similarly to the instrument trays, the lid is preferably also constructed with outward cranked lateral walls.

In a further embodiment of the device according to the invention the lid and each instrument tray are constructed with a rectangular horizontal outline and manufactured from a synthetic material which is impact resistant and can be sterilised by steam, preferably from PPSU (polyphenylene sulfone). The instrument trays are preferably produced by deep drawing, thus obtaining a greater strength.

In another embodiment of the device according to the invention the cover plate of the lid and the bases of the instrument trays are provided with ventilation holes, by virtue of which the surgical instruments and the implants stored in the device can be sterilised. The ventilation holes have a diameter between 3 mm and 8 mm, preferably 6 mm. In this embodiment of the device according to the invention the depth $T_D$ on the outward cranked lateral walls on the lid and the depths $T_i$ on the outward cranked lateral walls on the instrument trays are to be so dimensioned, that when the lid is placed on and the instrument trays are stacked, the lower locking elements rest on the upper locking elements of the respective instrument tray adjacent below and due to this the shoulders on the lateral walls are not resting on the bases of the instrument tray adjacent below. The air gap produced by this between the upper and lower instrument tray supports the ventilation during the sterilising process.

Each locking mechanism preferably comprises a first rod-shaped slide and each locking means a second rod-shaped slide. The slides have a longitudinal axis that runs parallel to the narrow side and parallel to the horizontal outline of the cover plate or of the base and can be displaced parallel to this longitudinal axis. The upper locking elements are constructed as recesses on the slides facing the upper side and perpendicular to the longitudinal axis, while the lower locking elements are provided on the underside of the slide as corresponding protuberances. The base of each instrument tray comprises locking holes passing through perpendicularly to the horizontal outline, through which the lower locking elements can be passed. The lower locking elements have slots extending parallel to the longitudinal axis; said slots can be engaged with the base of the instrument tray adjacent below by displacing the slide via the lower locking elements guided through the locking holes of an instrument tray adjacent below.

In a further embodiment of the device according to the invention the bases of the instrument trays have cavities on the upper side, the shape of which defines the surgical instrument and/or implant intended for each cavity. The cavities have a correspondingly determined depth, which together with the dimensions $H_i$ and $T_i$ of the upper instrument tray of two instrument trays stacked together are so determined, that the surgical instruments or implants placed into the cavities in a defined manner of the lower instrument tray can be secured perpendicularly to the base by the bottom areas of the cavities of the upper instrument tray. In this case the instrument trays can be stacked only in a defined sequence.

With their bases and cavities the instrument trays have a three-dimensional structure, by virtue of which an additional resistance of the instrument tray to twisting is achieved.

Further advantageous developments of the invention are characterised in the dependent claims.

The advantages achieved by the invention can be basically seen in that thanks to the device according to the invention no outer shell is required, resulting in less storage area in the operating theatre. Furthermore, due to the lack of the outer shell a better ventilation of the device is achieved in the case of a sterilisable execution.

In the following the invention and developments of the invention are explained in detail based on the partly schematic illustrations of a plurality of embodiments.

Figure 2:
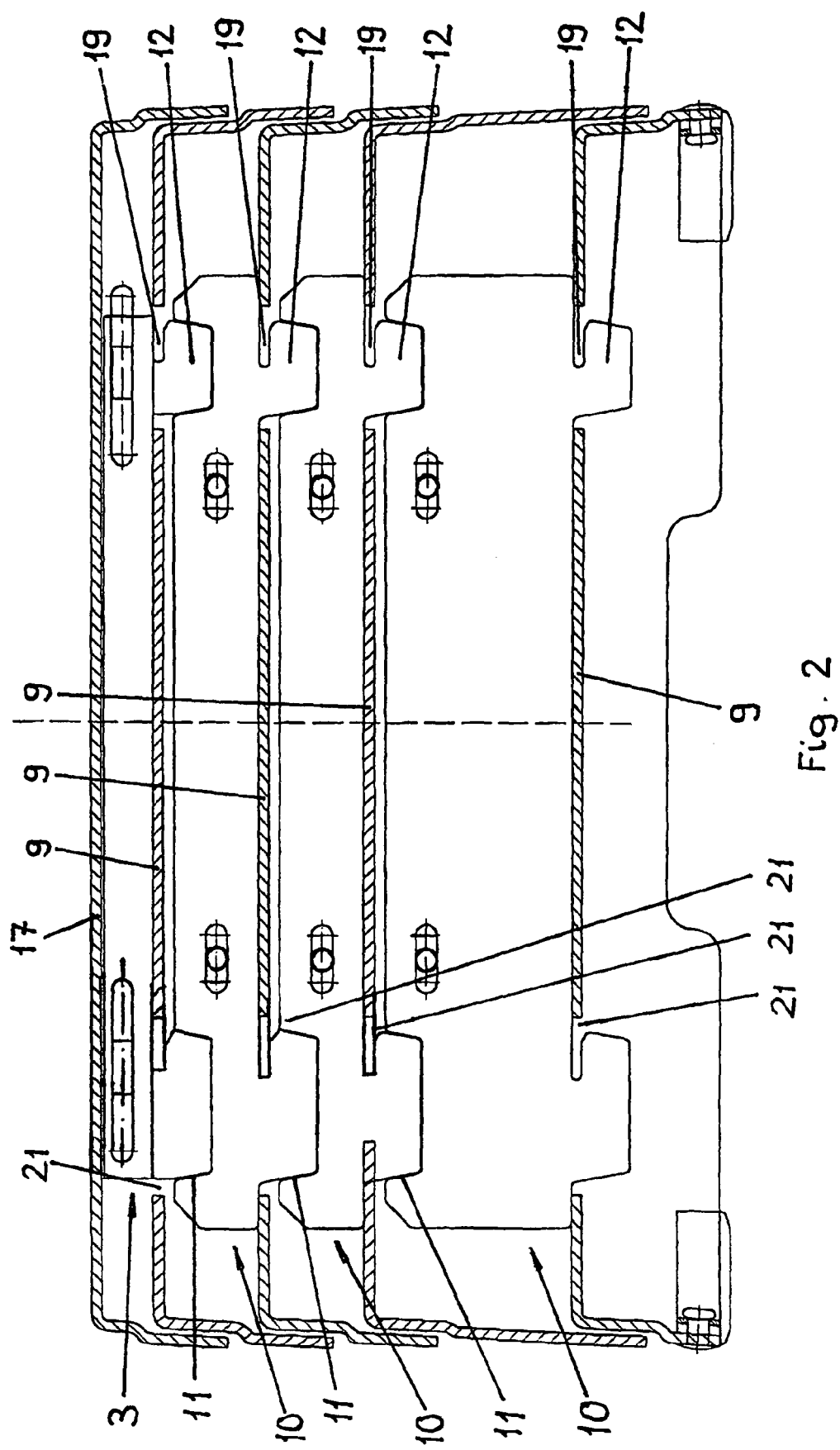
Figure 3:
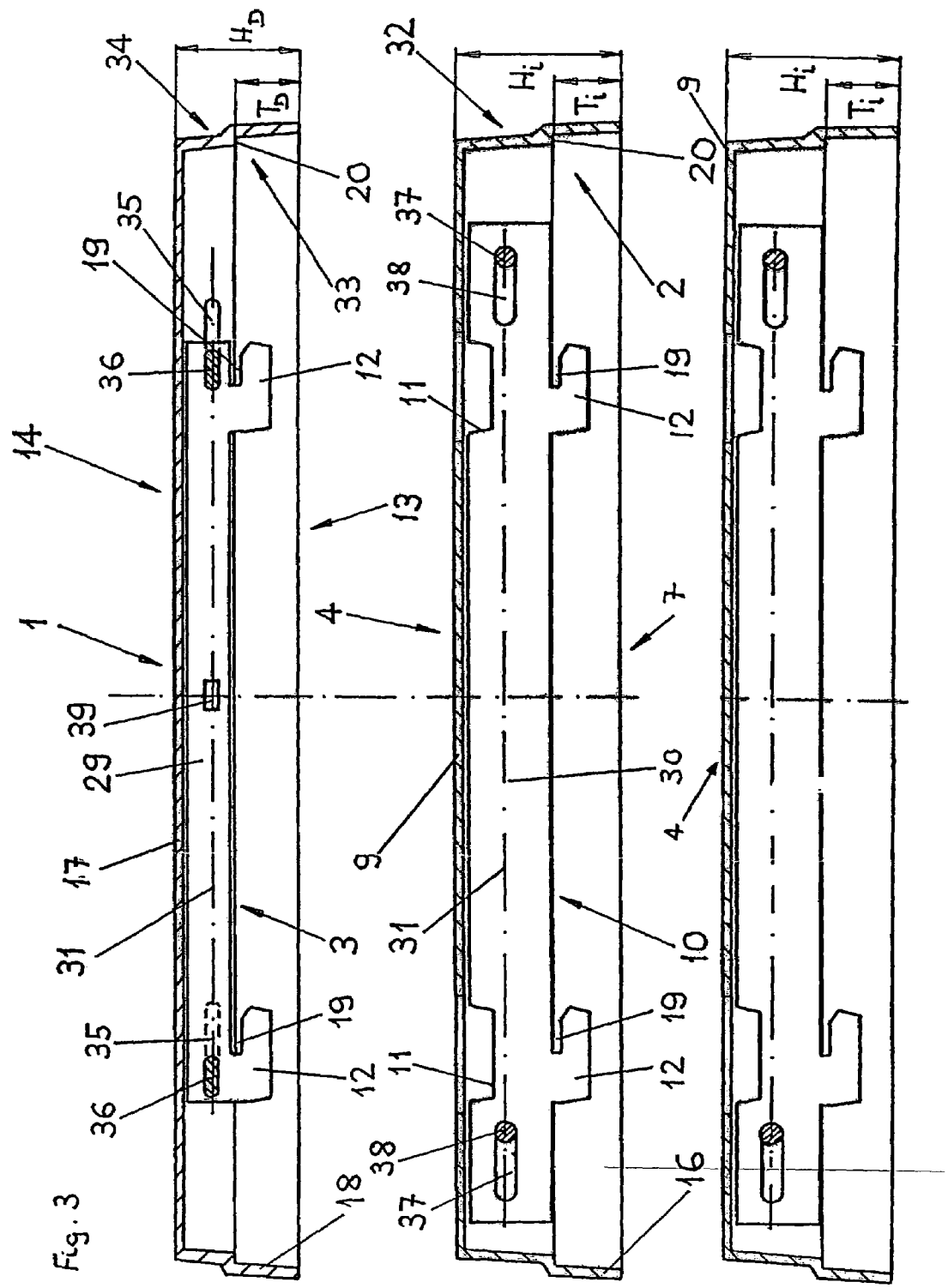
Figure 4:
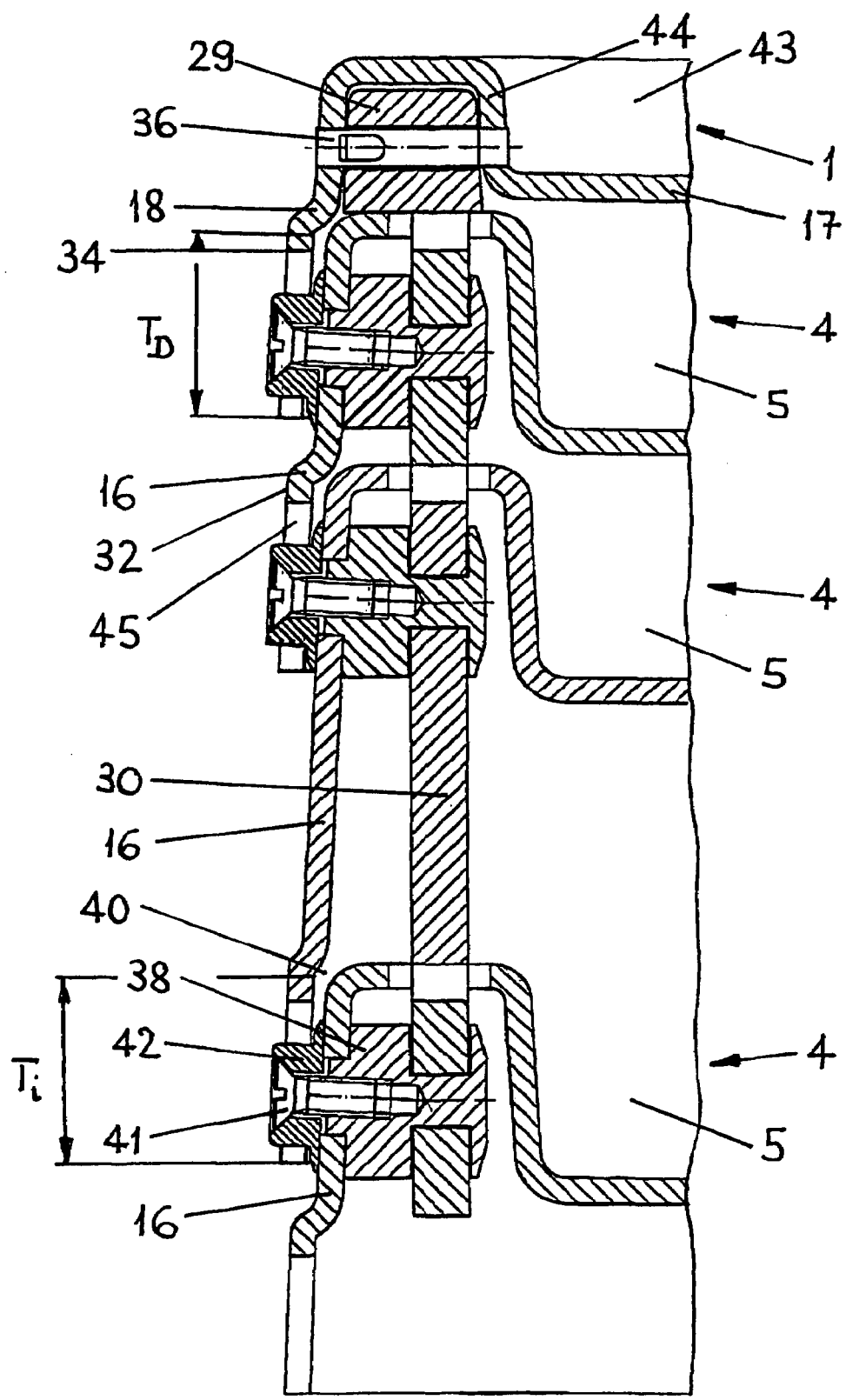
Figure 5:
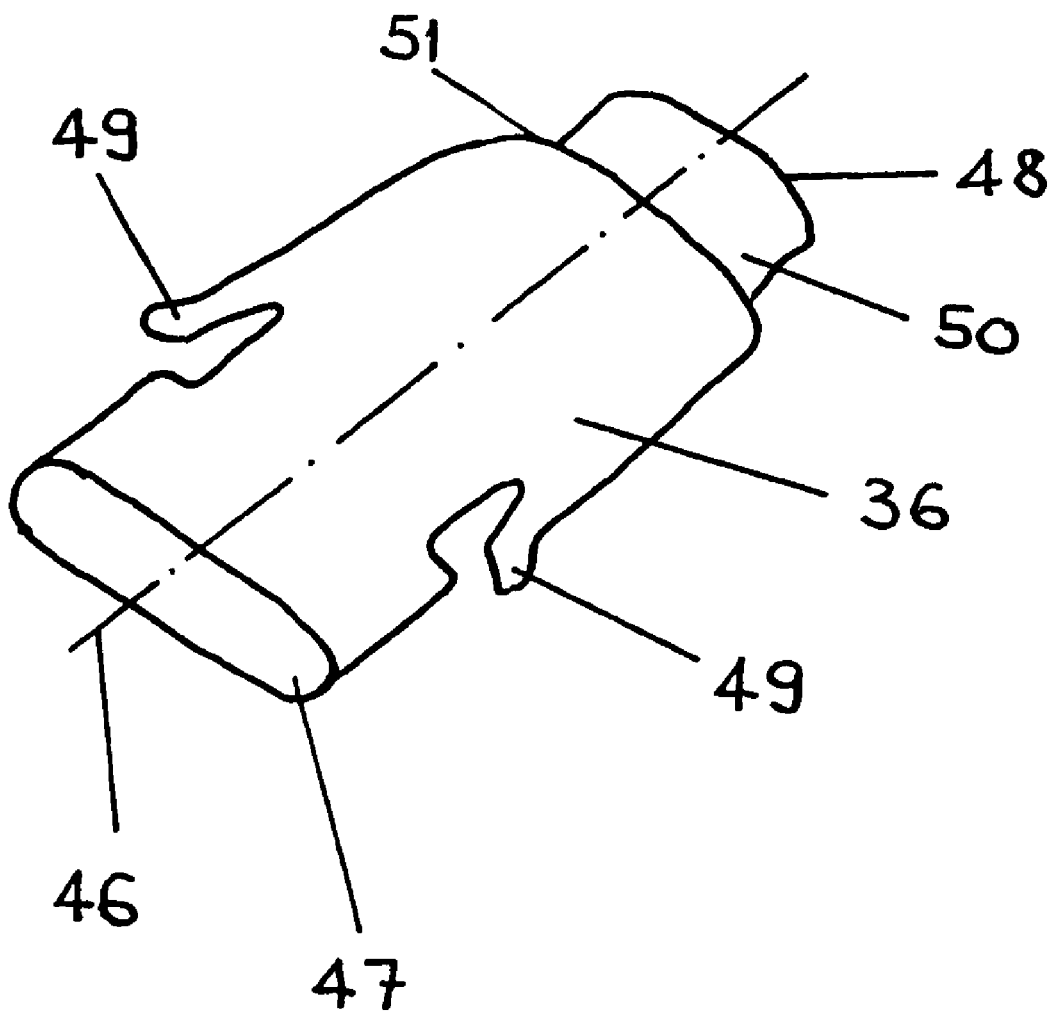

They show in:

FIG. 1—a perspective illustration of an embodiment of the device according to the invention with a lid and four instrument trays, FIG. 2—a section (section A—A according to FIG. 1) parallel to the narrow sides of the embodiment illustrated in FIG. 1 of the device according to the invention, FIG. 3—a section (section A—A according to FIG. 1) parallel to the narrow sides of the embodiment illustrated in FIG. 1 of the device according to the invention with a lid and an instrument tray, FIG. 4—a section through the lateral walls parallel to the longitudinal sides of an embodiment of the device according to the invention, and FIG. 5—a perspective illustration of a guide spigot of an embodiment of the device according to the invention.

FIG. 1 shows an embodiment of the device according to the invention with four instrument trays 4 and a lid 1, wherein the lid 1 and the instrument trays 4 have a rectangular horizontal outline with two parallel narrow sides 27 and two also parallel longitudinal sides 25. The instrument trays 4 have a shell-shaped design and are stackable. Each instrument tray 4 has a base 9, an upper side 6 that is parallel to the base 9, an underside 7 and lateral walls 16 on the entire circumference of the horizontal outline, said walls standing on the base 9 perpendicularly on the underside 7 of the instrument tray 4. The lid 1 has a cover plate 17 having the same horizontal outline as the bases 9 of the instrument trays 4, as well as a lid top side 14, a lid underside 13 and lateral walls 18 on the entire circumference of the horizontal outline, said walls standing on the cover plate 17 perpendicularly on the lid underside 13. Furthermore, two handles 26 that can pivot about the axles of rotation 22 arranged perpendicularly to the cover plate 17 are provided on the narrow sides 27 of the lid 1 for the purpose of operating the locking mechanisms 3 (FIGS. 2 and 3) as well as two carrier handles 23.

Each instrument tray 4 has an n number of cavities 5, each having a depth of $T_j$ (j=1 to n) and a base area ($G_j$; j=1 to n) 8, to accommodate the surgical instruments and/or implants. The shapes of the cavities 5, determined by the base areas ($G_j$; j=1 to n) 8 and the depths $T_j$ (j=1 to n) are determined optimally in consideration of the external contours of the surgical instrument or implant allocated to each cavity 5, by virtue of which a falling off or a mutual contacting of the instruments or implants placed therein will be prevented. The arrangement of the cavities 5 and, consequently, of the contents on each instrument tray 4 is carried out preferably to suit the progress of the operation that determines the sequence of the instruments and/or implants to be used. The preparation of the entire contents in the device according to the invention is considerably facilitated by this accurate allocation of the individual cavities 5 for the subsequent use in the operating theatre, since it can be very quickly determined by a single visual checking whether the entire system is complete.

At the same time the height $H_i$ (FIG. 3) of an instrument tray (i) 4 as well as the depths $T_j$ (j=1 to n) of the n cavities 5 are so determined, that the surgical instruments and/or implants placed into the allocated cavities 5 in the instrument tray (i) 4 can be secured by the base areas 8 of the instrument tray (i−1) 4 adjacent above perpendicularly to the base areas 8. By virtue of this the falling out of the surgical instruments and/or implants from the cavities 5 will be prevented when the device is shaken. Furthermore, the lateral walls 16 have an outward crank from the underside 7 to a depth of $T_i$, so that a shoulder 20 will be formed on the inside 2 which, when the instrument trays (i) 4 are stacked, rests on the base 9 of the instrument tray (i+1) 4 adjacent below.

On the narrow sides 27 of each instrument tray 4 there are two locking holes 21 provided to accommodate the lower locking elements 12 (FIGS. 2 and 3). In the sterilisable embodiment of the invention the cover plate 17, bases 9 and the base areas 8 of the cavities 5 have ventilation holes 24, having preferably a diameter of 6 mm. The diameter of the ventilation holes 24 is determined by taking the smallest instruments and/or implants into consideration, so that these cannot fall out from the device or an instrument tray (i) 4 on to the instrument tray (i+1) 4 adjacent below. For a good ventilating effect during the sterilisation it is of advantage to have as many as possible ventilation holes 24.

FIG. 2 illustrates a lid 1 and four instrument trays 4 in the stacked state sectioned along A—A of FIG. 1.

FIG. 3 shows the lid 1 and an instrument tray (i) 4 sectioned (section A—A of FIG. 1) parallel to the narrow sides 27. The lateral walls 16 of the instrument tray 4 have an internal side 2, an external side 32 and a height $H_i$ allocated to the instrument tray (i) 4. The lateral walls 18 of the lid 1 have an internal side 33, an external side 34 as well as a height of $H_D$ and have an outward crank from the lid underside 13 to a depth of $T_D$, so that similarly to the instrument tray 4 a shoulder 20 is formed to rest on the base 9 of the instrument tray 4 adjacent below.

FIGS. 2 and 3 show the locking mechanism 3 on the lid 1 that can be displaced parallel to the cover plate 17 as well as the locking means 10 on the instrument trays 4 which can be displaced parallel to the bases 9, while on each of the two narrow sides 27 (FIG. 1) one locking mechanism 3 each as well as one locking means 10 for each instrument tray 4 is provided. The locking mechanism 3 comprises two lower locking elements 12 facing the lid underside 13 for the purpose of fastening the lid 1 on the uppermost instrument tray (i=1) 4, while the locking elements 10 comprise two upper locking elements 11 facing the top side 6 and two lower locking elements 12 directed against the underside 7. The lower locking elements 12 have a shape that is complementary to the upper locking elements 11. When stacking a plurality of instrument trays as well as when placing on the lid 1, the lower locking elements 12 can be guided through the locking holes 21 provided in the instrument trays 4 and can be engaged in a form-locking manner perpendicularly to the bases 9 with the upper locking elements 11 of the respective instrument tray 4 adjacent below. Consequently, by moving the locking mechanisms 3 the locking means 10 of all instrument trays 4 stacked above one another will be also moved.

The locking mechanisms 3 are constructed as a first bar-shaped slide 19 and the locking means 10 as a second bar-shaped slide 30. The slides 29, 30 have a longitudinal axis 31 that is parallel to the narrow sides 27 as well as parallel to the horizontal outline of the cover plate 17 and of the bases 9. On the narrow sides 27 (FIG. 1) of the lateral walls 18, parallel to the longitudinal axis 31, two guide grooves 35, constructed as slots, are constructed, whereby two guide spigots 36 fitted to the first slide 29 are so inserted, that the slides 29 are joined with the lid 1 displaceably parallel to the longitudinal axis 31. The second slides 30 on the instrument trays 4 are provided with slots 37 that are also parallel to the longitudinal axis 31, in which the guide elements 38 fastened on the lateral walls 16 are accommodated, so that the second slides 30 are joined with the instrument trays displaceably parallel to the longitudinal axis 31. By means of a lug 39 on the first slide 3, which lug is engaged by the handle 26 (FIG. 1), the pivoting movement of the handle 26 (FIG. 1) is transmitted into a linear movement extending parallel to the longitudinal axis 31.

In the preferred embodiment of the device according to the invention the construction of the locking means 10 is so executed that on the slides 29, 30 the lower locking elements 11 are provided as wedge-shaped protuberances projecting perpendicularly to the longitudinal axis 31 and the upper locking elements 12 also as wedge-shaped recesses extending perpendicularly to the longitudinal axis 31. Each of the lower locking elements 11, executed as protuberances, has a groove 19. When locking the locking mechanisms 3 by rotating the handle 26, the slides 29, 30 are displaced parallel to the longitudinal axis 31, due to which the grooves 19 on the lower locking elements 11 constructed as protuberances will engage the base 9 of the respective instrument tray 4 adjacent below and the lid 1 will be secured with the uppermost instrument tray (i=1) 4 as will be the instrument trays (i=1 to z) adjacent below relative to one another.

FIG. 4 shows a section parallel to the longitudinal sides 25 through the lateral walls 16, 18 of an embodiment of the device according to the invention combined from a lid 1 and three instrument trays 4. The lid has on its top side 14 an indentation 43, so that the cover plate 17 has a depth and the lid 1 has an additional internal wall 44. In contrast to the embodiment of the device according to the invention illustrated in FIG. 3 the guide grooves 35 (FIG. 3) are executed as slots on the first slide 29, while guide spigots 36, mounted in oval holes in the lateral wall 18 and the internal wall 44 of the lid 1, are used for the purpose of displaceable mounting of the first slide 29 on the lid 1. The displaceable mounting of the second slide 30 on the instrument tray 4 is so constructed, that the second slides 30 have slots 37 (FIG. 3) and guide elements 38 fastened on the lateral wall 16 by means of an intermediate ring 42 and a screw 41 serve as mounting spigots, accommodated in the slots 37, for the second slides 30. In the embodiment of the device according to the invention illustrated here the depths $T_D$ and $T_i$ are so chosen, that when the lid 1 is placed on or when the instrument trays 4 are stacked, the first and second slides 29, 30 stand on top of one another, so that between the lid 1 and the instrument tray 4 adjacent below as well as between the individual instrument trays 4 an air gap 40 remains. The intermediate rings 42 are basically perpendicular to the lateral walls 16 and consequently form cogs protruding from the external side 32 through the lateral walls 16; when placing the lid 1 on the uppermost instrument tray 4 or when stacking several instrument trays 4 these cogs can engage the openings 45 provided in the lateral walls 16, 18 and are open towards the underside 7. At the same time the intermediate rings 42 may have various outside diameters, so that by a complementary construction of the openings 45 in the lateral walls 16 the lid 1 and the instrument trays 4 can be stapled only according to an arrangement defined by the narrow sides 27 or the longitudinal sides 25 and cannot be rotated, for example, about 180°.

FIG. 5 shows a guide spigot 36 of the embodiment of the device according to the invention illustrated in FIG. 4. The guide spigot 36 has a central axis 46, an external end 47 directed towards the external side 34 (FIG. 3) and an axially opposite inserted inner end 48. The cross-section perpendicularly to the central axis 46 is oval. On the inner end 48 the guide spigot 36 further comprises a pin also having an oval cross-section, that has semi-axes which are smaller than those of the external end 47, thus forming a shoulder 51. Two baffles 49, protruding in the direction of the large semi-axis of the cross-section, serve the purpose of fastening the guide spigot 36 in the lid 1.

What is claimed is:

1. A device for storing surgical instruments and/or implants, comprising:
    A) upper and lower shell-shaped instrument trays (4), each instrument tray comprising a base (9), an upper side (6), an underside (7), and lateral walls (16), wherein said upper side is essentially parallel to a horizontal outline of the base (9), said lateral walls (16) extending generally perpendicularly relative to the base (9), and wherein said upper instrument tray is adapted to be stacked on said lower instrument tray; and
    B) a lid (1) comprising a cover plate (17) having a horizontal outline identical to the base horizontal outline, an upper side (14), an underside (13), and at least one displaceable locking mechanism (3), said locking mechanism detachably fastening the lid (1) on the upper side (6) of one of said upper and lower instrument trays;
    C) each of said instrument trays comprises locking means (10) that is operable to detachably fasten each of said instrument trays to an immediately subjacent instrument tray; wherein:
    D) the locking means (10) comprise upper locking elements (11) facing the upper side (6) of the associated instrument tray and lower locking elements (12) facing the underside (7) of the associated instrument tray;
    E) the locking mechanism (3) also comprises lower locking elements (12) facing the lid underside (13); and wherein
    F) the lower locking elements (12) can be detachably engaged with the upper locking elements (11) of the immediately subjacent instrument tray and the locking elements (11, 12) are synchronously displaced by displacing the at least one locking mechanism (3) on the lid (1).

2. The device according to claim 1, wherein the lower locking elements (12) can be detachably engaged with the base (9) of the immediately subjacent instrument tray by displacing the locking mechanism (3) parallel to the horizontal outline.

3. The device according to claim 2, wherein the at least one locking mechanism (3) comprises a handle (26) to displace the locking mechanism (3).

4. The device according to claim 1, wherein the lateral walls (16) of the instrument trays (4) have a height ($H_i$), an internal side (2), and an external side (32), said lateral walls being disposed on the underside (7) and are outwardly cranked from the underside (7) to a depth of ($T_i$), so as to form a shoulder (20) on the lateral wall internal side (2).

5. The device according to claim 1, wherein the horizontal outline of the cover plate (17) and of each base (9) is essentially rectangular and comprises two parallel longitudinal sides (25) and two parallel narrow sides (27), while two locking mechanisms (3) are provided on the lid (1) and two locking means (10) are provided on each instrument tray (4), said locking mechanisms and said locking means being aligned with the narrow sides (27).

6. The device according to claim 4, wherein a depth ($T_i$) of each instrument tray is dimensioned so that the shoulder (20) can rest on the base (9) of the immediately subjacent instrument tray.

7. The device according to claim 4, wherein a depth ($T_i$) of each instrument tray is dimensioned so that when the instrument trays (4) are stacked an air gap (40) remains between the shoulders (20) on the lateral walls (16) and the bases (9) of the immediately subjacent instrument tray.

8. The device according to claim 1, wherein ventilation holes (24) are formed in the cover plate (17) and each base (9), said ventilation holes extending perpendicularly through the cover plate and each base.

9. The device according to claim 5, wherein each locking mechanism (3) comprises a first bar-shaped slide (29) and each locking means (10) comprises a second bar-shaped slide (30), said first and second slides (29, 30) defining a longitudinal axis (31) that extends parallel to the narrow side (27) and parallel to the horizontal outline of the cover plate (17) or base (9).

10. The device according to claim 9, wherein the upper locking elements (11) are provided on the slides (30) as recesses extending perpendicular to the longitudinal axis (31) and the lower locking elements (12) are provided on the slides (29, 30) as corresponding protuberances, the base (9) comprises locking holes (21) passing perpendicularly to the horizontal outline through which the lower locking elements (12) can be passed, and the lower locking elements (12) include a slot (9) extending parallel to the longitudinal axis (31), said slot being engaged with the base (9) of the immediately subjacent instrument tray (4) by displacing the slide (29, 30) via the lower locking elements (12) guided through the locking holes (21) of the immediately subjacent instrument tray (4).

11. The device according to claim 4, wherein the base (9) of each instrument tray comprises n cavities (5) on the upper side (6), the shape of each cavity (5) defining a surgical instrument and/or implant intended for storage, said cavities having a depth ($T_j$) and a base area ($G_j$), and wherein the height and depth dimensions (Hi, Ti) of an upper one of two instrument trays (4) stacked on top of one another and the depths ($T_j$) of a lower and upper instrument tray (4) are selected so that the surgical instruments or implants placed into the cavities (5) of the lower instrument tray (4) in a determined manner can be secured perpendicularly to the base (9).

12. The device according to claim 9, wherein the second slides (30) have slots (37) that are parallel to the longitudinal axis (31) and guide elements (38) fastened on the lateral walls (16) by cooperation of an intermediate ring (42) and a screw (41) serve as mounting spigots for the second slide (30), said second slide being adapted to be accommodated in the slots (37), said intermediate ring (42) being essentially perpendicular on the lateral walls (16) and consequently form lugs protruding past the lateral walls (16), said lugs being engaged by the openings (45) on the lateral walls (16) open to the underside (7) when the lid (1) is placed on an uppermost instrument tray (4) or when stacking a plurality of instrument trays (4).

* * * * *